United States Patent
Kim et al.

(10) Patent No.: US 9,995,379 B2
(45) Date of Patent: Jun. 12, 2018

(54) DRIVING MODULE AND MOTION ASSISTANCE APPARATUS INCLUDING THE SAME

(71) Applicant: Samsung Electronics Co., Ltd., Suwon-si, Gyeonggi-do (KR)

(72) Inventors: Jeonghun Kim, Hwaseong-si (KR); Hyun Do Choi, Yongin-si (KR); Se-Gon Roh, Suwon-si (KR); Minhyung Lee, Anyang-si (KR); Youn Baek Lee, Suwon-si (KR); Jongwon Lee, Uiwang-si (KR); Byungjune Choi, Gunpo-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 233 days.

(21) Appl. No.: 14/741,167

(22) Filed: Jun. 16, 2015

(65) Prior Publication Data
US 2016/0215864 A1 Jul. 28, 2016

(30) Foreign Application Priority Data

Jan. 22, 2015 (KR) .......................... 10-2015-0010589

(51) Int. Cl.
*F16H 29/02* (2006.01)
*F16H 25/20* (2006.01)
(Continued)

(52) U.S. Cl.
CPC .............. *F16H 25/20* (2013.01); *A61F 2/60* (2013.01); *A61H 3/00* (2013.01); *F16H 19/0622* (2013.01);
(Continued)

(58) Field of Classification Search
CPC .......... A61H 2201/1676; A61H 1/0262; A61H 2201/1207; A61H 2201/1238; A61H 2201/149; A61H 2201/1628; A61H 2201/164; A61H 2201/1669; F16H 25/20; F16H 19/0622; A61F 2/60
See application file for complete search history.

(56) References Cited

U.S. PATENT DOCUMENTS 5,282,460 A * 2/1994 Boldt ........................ A61F 2/68
403/119
5,399,154 A * 3/1995 Kipnis .................. A61F 5/0125
602/16
(Continued)

FOREIGN PATENT DOCUMENTS

JP  1995112035  2/1995
JP  3530959 B2  5/2004
(Continued)

*Primary Examiner* — Zakaria Elahmadi
(74) *Attorney, Agent, or Firm* — Harness, Dickey & Pierce, P.L.C.

(57) ABSTRACT

A driving module including a driving source configured to generate power, a rotary rod connected to the driving source to rotate by receiving the power from the driving source, a power conversion block coupled with the rotary rod to be straight-line-driven in a longitudinal direction of the rotary rod in response to a rotation of the rotary rod, and a power transmission unit configured to operate in response to a driving of the power conversion block is disclosed.

17 Claims, 9 Drawing Sheets

(51) Int. Cl.
  *A61F 2/60*  (2006.01)
  *F16H 19/06*  (2006.01)
  *A61H 3/00*  (2006.01)
  *A61H 1/02*  (2006.01)

(52) U.S. Cl.
  CPC .... *A61H 1/0262* (2013.01); *A61H 2201/1207* (2013.01); *A61H 2201/1238* (2013.01); *A61H 2201/149* (2013.01); *A61H 2201/164* (2013.01); *A61H 2201/165* (2013.01); *A61H 2201/1628* (2013.01); *A61H 2201/1669* (2013.01); *A61H 2201/1676* (2013.01); *F16H 2025/2096* (2013.01)

(56) References Cited

U.S. PATENT DOCUMENTS

| | | | | |
|---|---|---|---|---|
| 7,041,074 | B1* | 5/2006 | Averianov | A61F 5/0102 128/845 |
| 7,220,231 | B2 | 5/2007 | Ashihara et al. | |
| 7,416,565 | B1* | 8/2008 | Al-Turaikl | A61F 2/60 623/52 |
| 7,574,939 | B2* | 8/2009 | Garrec | B25J 9/104 74/490.03 |
| 8,652,075 | B2* | 2/2014 | Takahashi | A61H 1/0244 601/34 |
| 2002/0026131 | A1* | 2/2002 | Halperin | A61H 9/0078 601/41 |
| 2003/0195442 | A1* | 10/2003 | Dyck | A61H 37/00 601/84 |
| 2009/0294187 | A1* | 12/2009 | Lee | A63H 11/00 180/8.6 |
| 2009/0308188 | A1* | 12/2009 | Yang | B25J 9/104 74/89.27 |
| 2010/0162846 | A1* | 7/2010 | Lee | B25J 9/1045 74/490.04 |
| 2010/0170357 | A1* | 7/2010 | Kim | B25J 9/102 74/89.32 |
| 2011/0056321 | A1* | 3/2011 | Sim | B25J 9/1025 74/490.04 |
| 2011/0167945 | A1* | 7/2011 | Yang | B25J 9/104 74/490.04 |
| 2012/0112485 | A1* | 5/2012 | Lee | B25J 15/0009 294/213 |
| 2014/0245846 | A1* | 9/2014 | Garrec | F16H 25/20 74/89.32 |
| 2014/0257336 | A1* | 9/2014 | Choi | A61B 19/2203 606/130 |

FOREIGN PATENT DOCUMENTS

| | | |
|---|---|---|
| JP | 2008068046 A | 3/2008 |
| JP | 4344314 B2 | 10/2009 |
| JP | 2009291395 A | 12/2009 |
| KR | 101247078 B1 | 3/2013 |

* cited by examiner

DRIVING MODULE AND MOTION ASSISTANCE APPARATUS INCLUDING THE SAME

CROSS-REFERENCE TO RELATED APPLICATION

This application claims the priority benefit of Korean Patent Application No. 10-2015-0010589, filed on Jan. 22, 2015, in the Korean Intellectual Property Office, the entire contents of which are incorporated herein by reference in its entirety.

BACKGROUND

1. Field

Example embodiments relate to driving modules and motion assistance apparatuses including the same.

2. Description of the Related Art

With the onset of rapidly aging societies, a number of people may experience inconvenience and pain from joint problems. Thus, there motion assistance apparatuses that may enable the elderly and patients having joint problems to walk with less effort may be desirable. Furthermore, there may be a desire for motion assistance apparatuses configured to increase the muscular strength of human bodies, for example, for use in military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and pedial frames disposed on feet of the users. The pelvic frames and femoral frames may be connected rotatably by hip joint portions, the femoral frames and sural frames may be connected rotatably by knee joint portions, and the sural frames and pedial frames may be connected rotatably by ankle joint portions.

The motion assistance apparatuses may include active joint structures including hydraulic systems and driving motors to drive each joint portion to improve muscular strength of legs of the users. For example, separate motors to transmit driving power may be provided at left and right hip joint portions, respectively.

SUMMARY

Some example embodiments relate to a driving module.

In some example embodiments, the module may include a driving source configured to generate power, a rotary rod connected to the driving source to rotate by receiving the power from the driving source, a power conversion block coupled with the rotary rod to be straight-line-driven in a longitudinal direction of the rotary rod in response to a rotation of the rotary rod, and a power transmission unit configured to operate in response to a driving of the power conversion block.

The module may further include a tensile force adjustment unit configured to connect the power conversion block and the power transmission unit, and adjust a tensile force of the power transmission unit.

The power transmission unit may include a first power transmission unit and a second power transmission unit, each connected to the tensile force adjustment unit, and the tensile force adjustment unit may include a winding member around which at least one of the first power transmission unit and the second power transmission unit is wound.

The module may further include a linear motion guide configured to guide a movement of the tensile force adjustment unit.

The module may further include a timing belt configured to rotate using the power generated by the driving source, and a rotary pulley driven by the timing belt to rotate the rotary rod.

A first screw thread may be formed on the rotary rod and a second screw thread corresponding to the first screw thread may be formed on the power conversion block.

Other example embodiments relate to a driving module.

In some example embodiments, the module may include a driving frame, a driving source configured to generate rotation power, a power conversion portion configured to convert the rotation power of the driving source into a straight-line motion, a power transmission unit configured to operate by receiving power from the power conversion portion, and a guide member configured to guide a movement of the driving frame.

The module may further include a tensile force adjustment unit coupled with the power transmission unit to adjust a tensile force of the power transmission unit, and the tensile force adjustment unit may include a winding member around which the power transmission unit is wound and a fixing member selectively coupled with the winding member to interfere in a rotation of the winding member.

An interferer of a polygonal shape may be formed on an upper end of the winding member and an indented portion of a shape corresponding to the interferer may be formed on the fixing member.

A recessed portion configured to accommodate the fixing member may be formed on the tensile force adjustment unit and the fixing member may be configured to slide in one direction in the recessed portion.

The winding member may include a first winding member and a second winding member, the power transmission unit may include a first power transmission unit and a second power transmission unit, and the first winding member may be coupled with the first power transmission unit and the second winding member may be coupled with the second power transmission unit.

The fixing member may include a first fixing member and a second fixing member, and the first fixing member and the second fixing member may be selectively combined with the first winding member and the second winding member, respectively.

The driving module may further include a tensile force adjustment unit coupled with the power transmission unit to adjust a tensile force of the power transmission unit, the power transmission unit may include a power transmission body and an insertion body attached to one side of the power transmission unit, the insertion body on which a first tensile force adjustment screw thread is formed, and the tensile force adjustment unit may include an adjustment body and an insertion body provided on at least one side of the adjustment body, the insertion body on which a second tensile force adjustment screw thread corresponding to the first tensile force adjustment screw thread is formed.

Other example embodiments relate to a motion assistance apparatus.

In some example embodiments, the apparatus may include a fixing module attached to a user and having an adjustable width, a driving module including a driving source, a power transmission unit configured to operate by receiving power from the driving source, and a tensile force adjustment unit coupled with the power transmission unit to adjust a tensile force of the power transmission unit, and a joint module configured to assist a motion of the user.

The joint module may be connected to the power transmission unit to operate by receiving power from the driving module.

The power transmission unit may further include a power transmission body, and a protection unit formed on at least a portion of the power transmission body.

The protection unit may include a rotary pulley configured to rotate in response to a driving of the power transmission body.

The protection unit may include a bent pipe configured to cover at least a portion of the power transmission body, and the bent pipe may include an accommodating space in which the rotary pulley is accommodated.

The protection unit may include a shaft including a flexible material and configured to cover at least a portion of the power transmission body.

The protection unit may include a surface body configured to cover at least a portion of the power transmission body and including a plurality of segment portions fluidly connected to one another.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
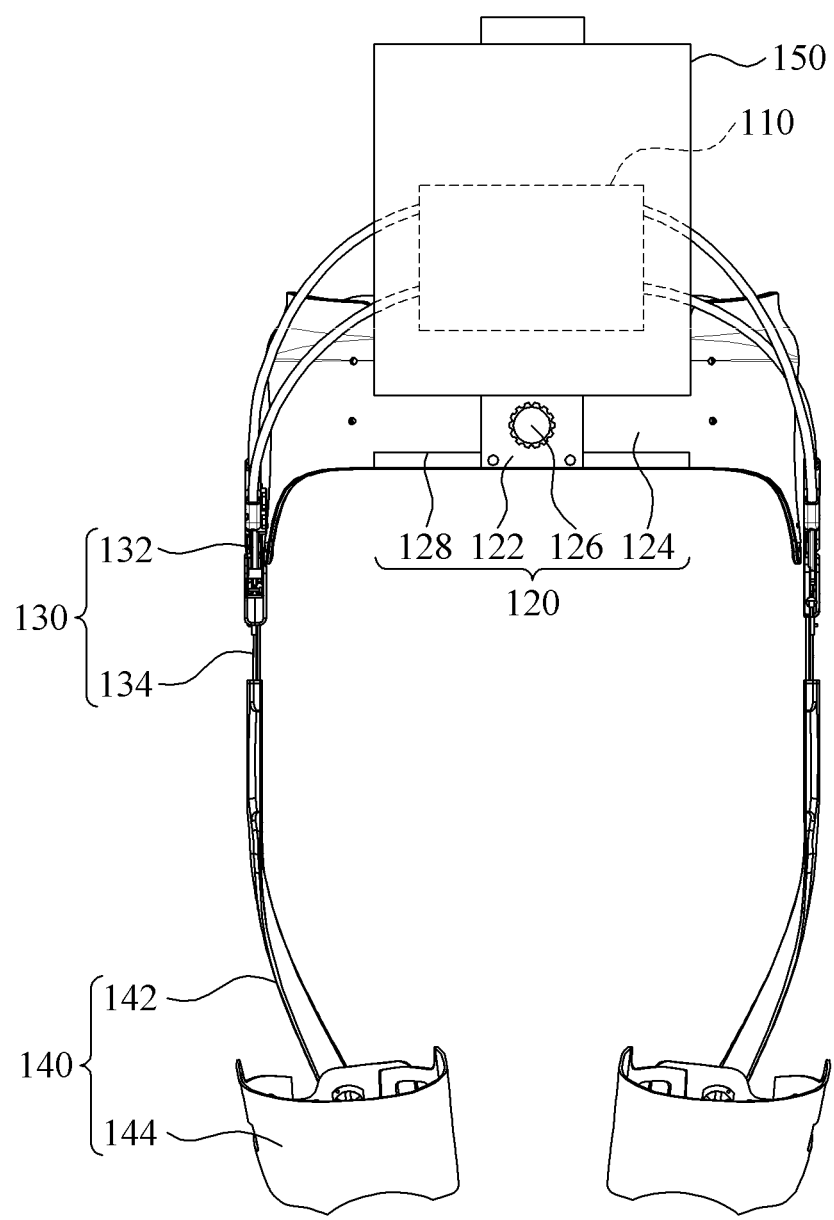
FIG. 1 a rear view illustrating a motion assistance apparatus according to example embodiments.

Various example embodiments will now be described more fully with reference to the accompanying drawings. Example embodiments, however, may be embodied in many different forms and should not be construed as being limited to the example embodiments set forth herein. Rather, these example embodiments are provided so that this disclosure will be thorough and complete, and will fully convey the scope of example embodiments to those skilled in the art. In the drawings, the sizes and relative sizes of various layers and regions may have been exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 2:
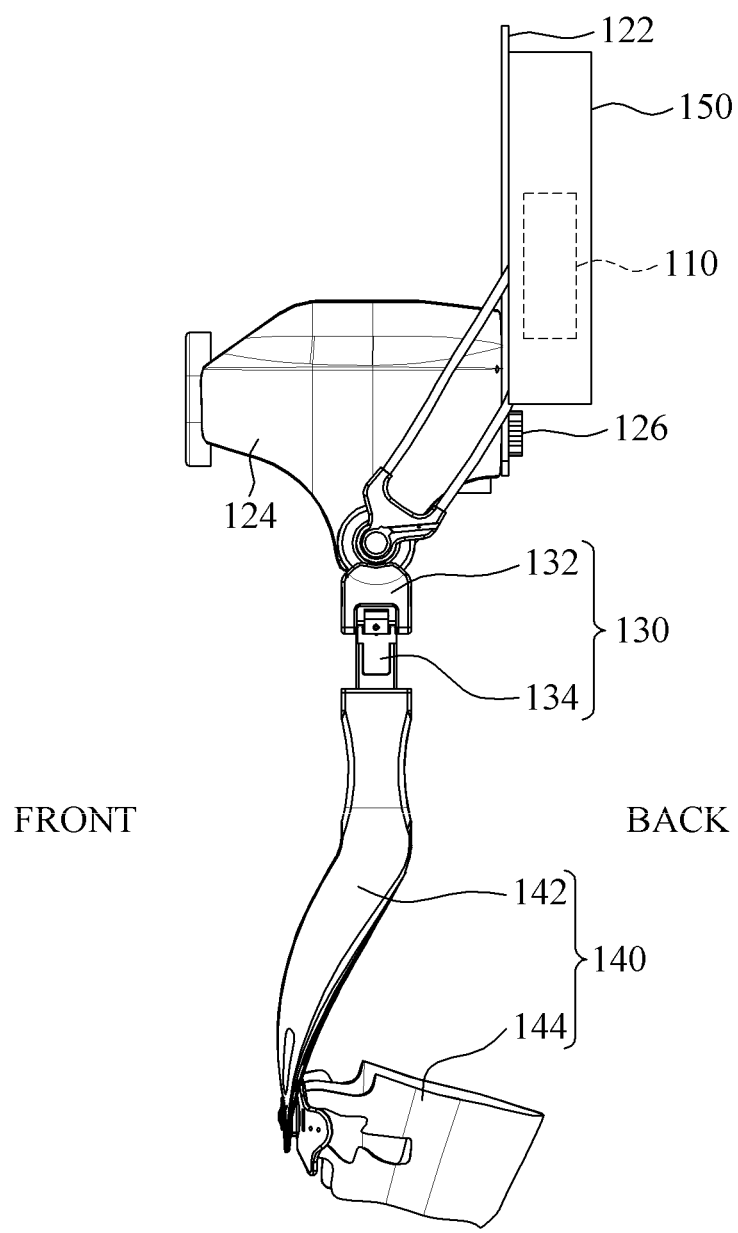
FIG. 2 is a side view illustrating a motion assistance apparatus according to example embodiments.

FIG. 1 is a rear view illustrating a motion assistance apparatus 100 according to example embodiments. FIG. 2 is a side view illustrating the motion assistance apparatus 100 according to example embodiments.

Referring to FIGS. 1 and 2, the motion assistance apparatus 100 may assist a motion of a user wearing the motion assistance apparatus 100. The user may be, for example, a human, an animal, or a robot. However, example embodiments are not limited thereto. Although FIG. 1 illustrates a case in which the motion assistance apparatus 100 assists a motion of a thigh of the user, the motion assistance apparatus 100 may assist a motion of another part of an upper body, for example, a hand, an upper arm, and a lower arm of the user, or a motion of another part of a lower body, for example, a foot, and a calf of the user. Thus, the motion assistance apparatus 100 may assist a motion of a part of the user.

Hereinafter, a case in which the motion assistance apparatus 100 assists a motion of a thigh of a human will be described as an example.

The motion assistance apparatus 100 may include a fixing module 120, a driving module 110, a joint module 130, and a supporting module 140.

The fixing module 120 may be attached to the user. The fixing module 120 may be in contact with at least a portion of an external surface of the user. The fixing module 120 may support a rear side of the user. A portion of the fixing module 120 may cover the external surface of the user. For example, the fixing module 120 may be attached to a back of the user while a portion of the fixing module 120 is covering a waist of the user.

The fixing module 120 may include a base body 122, a plurality of side frames 124, a dial 126, and a sliding guide 128. The base body 122 and the side frames 124 may cover a circumference of a body part of the user.

The base body 122 may support one side of the user. For example, the base body 122 may support the rear side of the user. The base body 122 may connect the plurality of side frames 124 together.

The side frames 124 may be disposed on both sides of the user. For example, the side frames 124 may support a left side and a right side of the waist of the user. The side frames 124 may include a left frame supporting the left side of the user and a right frame supporting the right side of the user. The side frames 124 may be provided in a form corresponding to the left side and right side of the user. The side frames 124 may be disposed symmetrically to one another based on the base body 122.

A space of the side frames 124 may be adjustable. The side frames 124 may be disposed farther from or close to one another based on a center of the base body 122. Accordingly, an entire width of the fixing module 120 may be adjusted. In this example, the fixing module 120 may also be used by a different user.

For example, the side frames 124 may be mounted to slide relative to the base body 122. A movement of the side frames 124 may be guided by forming the sliding guide 128 and inserting a guide protrusion formed on the base body 122 into the sliding guide 128.

Also, the space of the side frames 124 may be adjusted through a manipulation of the dial 126. In an example, the space of the side frames 124 may be adjusted based on a rack and pinion structure. A rack connected to the dial 126 may be engaged with a pinion formed on the side frames 124, thereby sliding the side frames 124. In another example, the side frames 124 may be connected to one another using a line member. In this example, the space of the side frames 124 may be adjusted by pulling and releasing the line member.

In still another example, the side frames 124 may include a hook and loop fastening member of which a length is adjustable. By changing an adhesion position of the hook and loop fastening member, the space of the side frames 124 may be adjusted. In yet another example, the base body 122 may include an elastic body. In this example, the base body 122 may be expanded based on a circumference of a target body, thereby adjusting the space of the side frames 124.

The driving module 110 may provide power transmitted to the joint module 130. The driving module 110 may be spaced apart from the joint module 130. Alternatively, the driving module 110 may be connected to the joint module 130. The driving module 110 may be mounted on a portion, for example, the base body 122, of the fixing module 120.

In some example embodiments, at least a portion of the driving module 110 may be accommodated in a box body 150. The box body 150 may be mounted on the base body 122 such that the driving module 110 is provided in a form of a backpack to be used on the back of the user. The driving module 110 may be, for example, a motor to generate power by receiving a voltage or a current.

The joint module 130 may receive the power from the driving module 110 to assist a motion of a joint region of the user. The joint module 130 may be disposed in a position corresponding to the joint region of the user. The joint module 130 may be disposed on the side frames 124. One side of the joint module 130 may be connected to the driving module 110, and another side may be connected to the supporting module 140.

The joint module 130 may include a rotary member 132 and a connection member 134.

The rotary member 132 may rotate based on the power transmitted from the driving module 110. The rotary member 132 may be disposed on one side of a hip-joint of the user.

The connection member 134 may connect the rotary member 132 and the supporting module 140. The connection member 134 may rotate based on rotation power of the rotary member 132. The connection member 134 may be coupled with the rotary member 132 using a separate coupling member, or may be formed as a single body with the rotary member 132. The connection member 134 may be connected with the supporting module 140 based on a hinge combination structure. Based on a hinge axis of the hinge combination structure and a rotation axis of the rotary member 132, the supporting module 140 may perform 2-degree-of-freedom movement relative to the fixing module 120.

The supporting module 140 may support a part of the user. The supporting module 140 may assist a motion of the part of the user. The supporting module 140 may rotate based on the power transmitted from the joint module 130. Rotation power of the supporting module 140 may be transmitted to the part of the user to assist the motion of the part of the target body.

The supporting module 140 may include a supporting frame 142 connected to the joint module 130 to rotate, and a supporting member 144 to cover the part of the target body.

Figure 3:
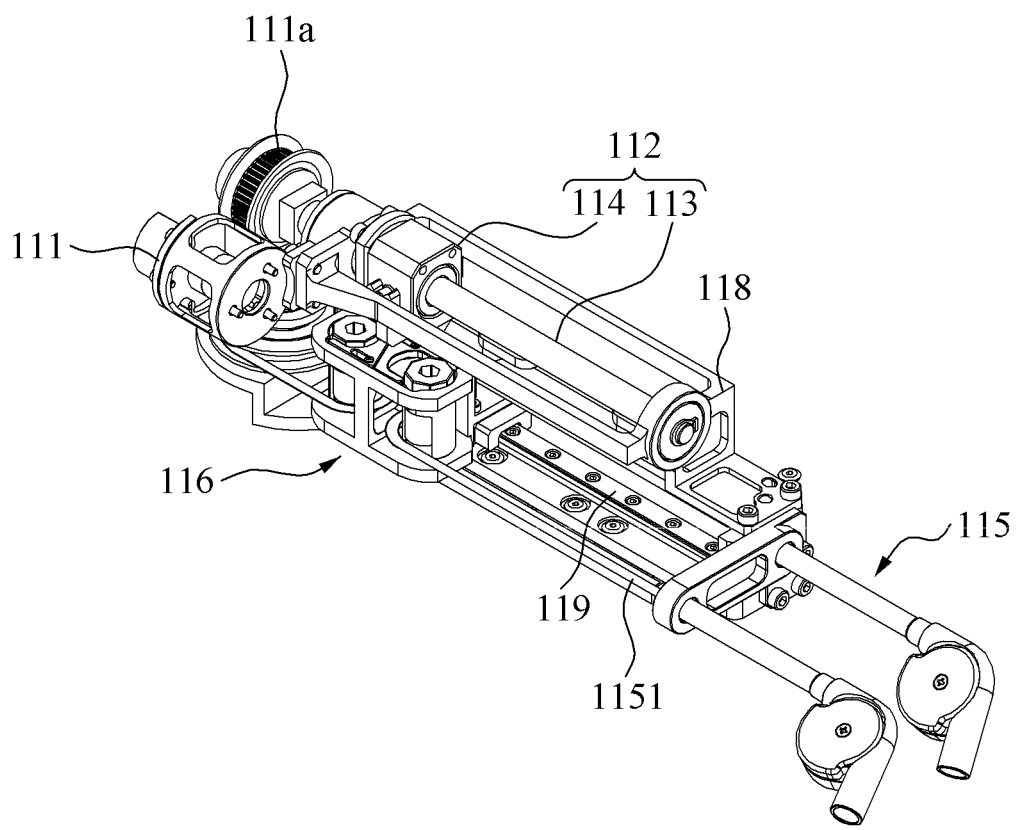
FIG. 3 is a perspective view illustrating a driving module according to example embodiments.

FIG. 3 is a perspective view illustrating the driving module 110 according to example embodiments.

Referring to FIG. 3, the driving module 110 may include a driving source 111, a power conversion unit 112, a power transmission unit 115, a tensile force adjustment unit 116, a driving frame 118, and a guide member 119.

The driving source 111 may include, for example, a motor to generate power by receiving a voltage or a current. Although the driving source 111 including the motor is described with reference to FIG. 3 as an example, a type of the driving source 111 is not limited thereto.

The power conversion unit 112 may convert rotation power of the driving source 111 into a straight-line movement. The power conversion unit 112 may include a rotary rod 113 and a power conversion block 114.

The rotary rod 113 may be connected directly or indirectly to the driving source 111, and may rotate by receiving power from the driving source 111. As an example, the rotary rod 113 may be indirectly connected to the driving source 111 using a driving pulley 111a connected with the driving source 111. In this example, the driving source 111 and the driving pulley 111a may be connected using a timing belt. The timing belt may be driven based on the power generated from the driving source 111. The driving pulley 111a may be driven using the timing belt, thereby driving the rotary rod 113 connected thereto. As another example, the rotary rod 113 may be directly connected to the driving source 111. The power conversion block 114 may be coupled with the rotary rod 113. The power conversion block 114 may be inserted to a circumference of the rotary rod 113. The power conversion block 114 may perform a straight-line driving in a longitudinal direction of the rotary rod 113 based on a rotation of the rotary rod 113.

The driving frame 118 may accommodate the rotary rod 113. The power conversion block 114 may perform the straight-line driving in the rotary rod 113.

In an example, a first screw thread may be formed on the rotary rod 113, and a second screw thread corresponding to the first screw thread may be formed on the power conversion block 114. For example, the first screw thread in a form of a male screw thread may be formed on an external surface of the rotary rod 113, and the second screw thread in a form of a female screw thread may be formed on a hole included in the power conversion block 114. In some example embodiments, the power conversion unit 112 may be provided in a form of a ball screw converting a rotation movement into a straight-line movement. In response to a rotation of the rotary rod 113, the power conversion block 114 may move along a screw thread of the rotary rod 113 so as to perform the straight-line driving in the longitudinal direction of the rotary rod 113.

The power transmission unit 115 may transmit the power received from the power conversion unit 112 to the joint module 130. The power transmission unit 115 may transmit the power based on, for example, a pulling or pushing force, a frictional force, a tensile force, and an elastic force.

The tensile force adjustment unit 116 may adjust a tensile force of the power transmission unit 115. For example, the tensile force adjustment unit 116 may be coupled with a power transmission body 1151 of the power transmission unit 115 and adjust a length of the power transmission body 1151, thereby adjusting the tensile force of the power transmission unit 115.

Figure 4A:
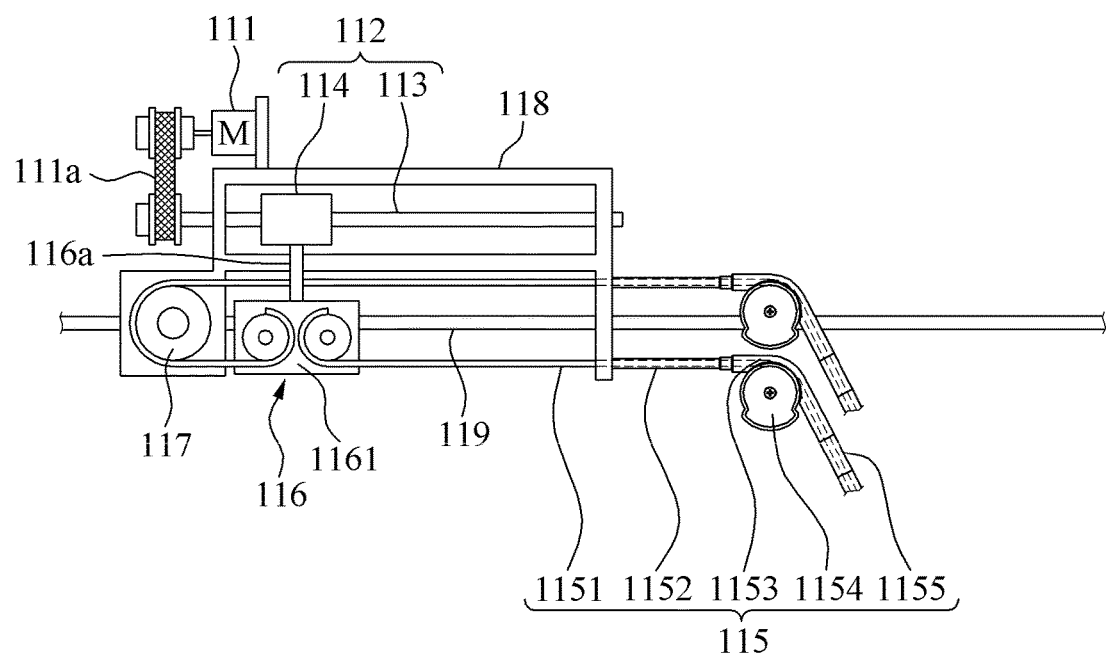
FIGS. 4A and 4B are cross-sectional views illustrating a driving module according to example embodiments.
Figure 4B:
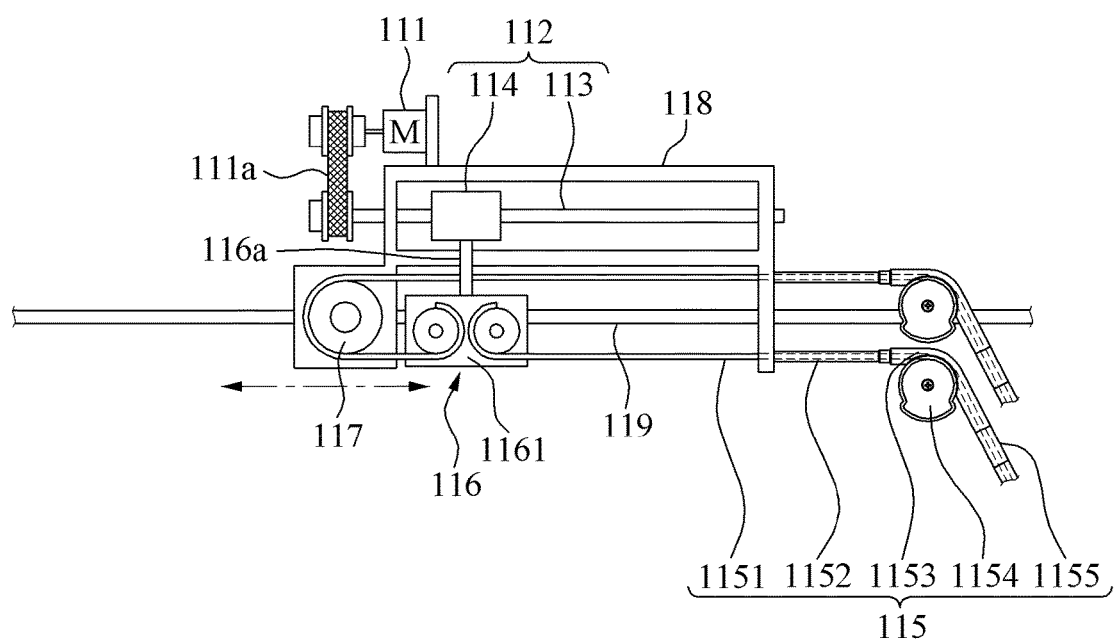

FIGS. 4A and 4B are cross-sectional views illustrating the driving module 110 according to example embodiments.

Referring to FIGS. 4A and 4B, the guide member 119 may be extended in a longitudinal direction of the driving frame 118. The driving frame 118 may move along the guide member 119. The driving source 111, the power conversion unit 112, the power transmission unit 115, and the tensile force adjustment unit 116 may be connected to the driving frame 118 to move along with the driving frame 118.

The driving frame 118 may maintain a tensile force of the power transmission unit 115 by moving along the guide member 119.

Conventionally, a space of a side frame may increase and a driving frame may not move in a motion assistance apparatus including a driving module 110. Therefore, a distance between the driving module and the joint module may increase. Accordingly, a tensile force greater than a desired (or, alternatively, a predetermined) reference tensile force may be applied to the power transmission unit 115.

In contrast, in one or more example embodiments, the driving frame 118 moves along the guide member 119 in a direction to be farther from the base body 122. Therefore, the distance between the driving module 110 and the joint module 130 may remain the same such that tensile force corresponding to the reference tensile force is applied to the power transmission unit 115.

Conversely, conventionally, when the space of the side frames decreases and the driving frame does not move, the distance between the driving module and the joint module may decrease. Accordingly, a tensile force less than the reference tensile force may be applied to the power transmission unit.

In contrast, in one or more example embodiments, the driving frame 118 moves along the guide member 119 toward the base body 122. Therefore, the distance between the driving module 110 and the joint module 130 may remain the same such that the tensile force corresponding to the reference tensile force is applied to the power transmission unit 115.

In one or more example embodiments, in response to the driving frame 118 actively performing a linear movement along the guide member 119 based on the space of the side frames 124, the tensile force of the power transmission unit 115 may be maintained to be constant. Through this, the motion assistance apparatus 100 may be prevented from abnormally operating or being damaged due to an abnormal tensile force applied to a power transmission module.

A power pulley 117 may be fixed to the driving frame 118 to rotate based on a movement of the tensile force adjustment unit 116. The power pulley 117 may be configured not to rotate in a process of moving the driving frame 118.

The tensile force adjustment unit 116 may connect the power conversion block 114 and the power transmission unit 115. The tensile force adjustment unit 116 may include an adjustment body 1161 and a connection body 116a. The adjustment body 1161 may be coupled with a power transmission body 1151, and the connection body 116a may connect the adjustment body 1161 and the power conversion block 114.

When the power conversion block 114 is driven, the tensile force adjustment unit 116 may be driven, and subsequently, the power transmission unit 115 may operate. The tensile force adjustment unit 116 may be driven along the guide member 119. The guide member 119 may include, for example, a linear motion guide. Although the guide member 119 including the linear motion guide is described as an example, a type of a guide member is not limited thereto.

Figure 5A:
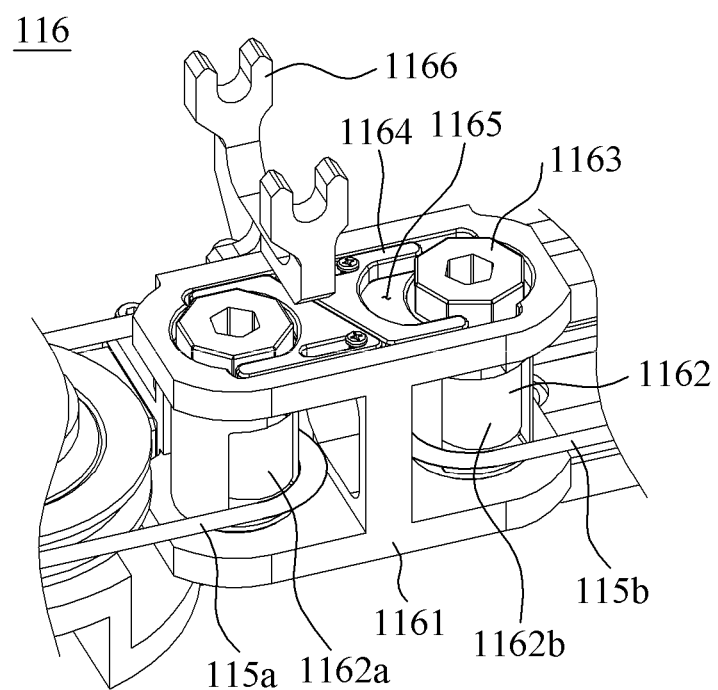
FIGS. 5A and 5B are perspective views illustrating a tensile force adjustment unit according to example embodiments.
Figure 5B:
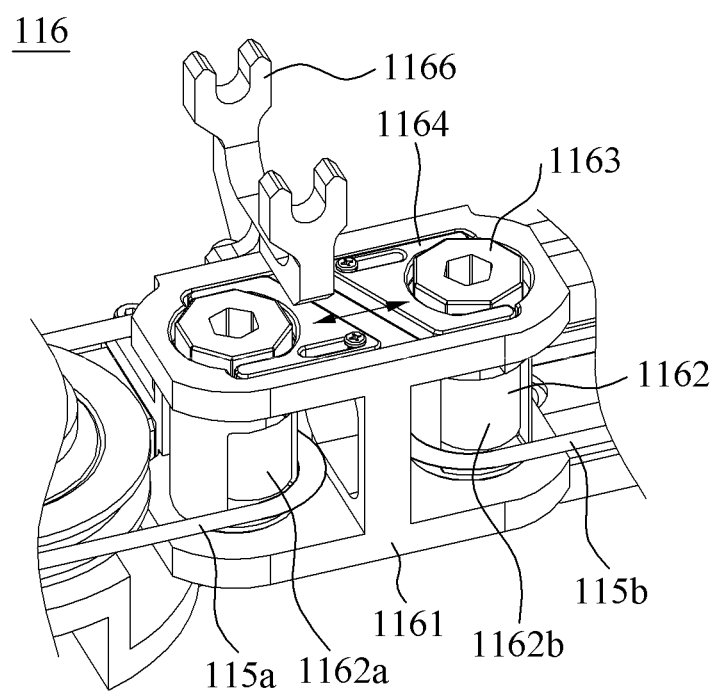

FIGS. 5A and 5B are perspective views illustrating the tensile force adjustment unit 116 according to example embodiments. FIG. 5A illustrates a form in which a portion of a fixing member 1164 is coupled with an interferer 1163 and FIG. 5B illustrates a form in which the fixing member 1164 is fully coupled with the interferer 1163.

Referring to FIGS. 5A and 5B, the tensile force adjustment unit 116 may adjust a tensile force of the power transmission unit 115.

The tensile force adjustment unit 116 may include the adjustment body 1161, a winding member 1162, and the fixing member 1164.

The adjustment body 1161 may accommodate the winding member 1162. The adjustment body 1161 may include a coupler 1166 coupled with the power conversion block 114. Based on the aforementioned configuration, when the power conversion block 114 is driven, the adjustment body 1161 may move along the guide member 119.

The winding member 1162 may be coupled with the power transmission unit 115, and may wind or release the power transmission unit 115 in a winding direction. The winding member 1162 may be provided in, for example, a form of a winch or a form of a capstan having a shape of a column. A portion of the winding member 1162 may be opened such that the power transmission unit 115 is inserted to the opened portion. However, the above description is provided as an example and thus, a type of the winding member 1162 is not limited thereto.

The winding member 1162 may include the interferer 1163 and the interferer 1163 may protrude from an upper end portion of the winding member 1162. The interferer 1163 may be formed in a shape of a polygonal column. The interferer 1163 may be provided in a shape of a nut. A hollow may be formed on a center of the interferer 1163. The hollow may have a cross section of a polygonal shape. For example, when the hollow has a cross sectional-shape of a hexagon, a user may wind the winding member 1162 by using an Allen wrench.

The winding member 1162 may be provided in a single or plural form. When the winding member 1162 is provided in a single form, the winding member 1162 may be coupled with at least one power transmission unit, for example, the power transmission unit 115. Also, the winding member 1162 provided in a single form may be coupled with a plurality of power transmission units including the power transmission unit 115. Alternatively, when the winding member 1162 is provided in a plural form, a plurality of winding members may be coupled with a plurality of power transmission units, respectively.

The fixing member 1164 may be selectively coupled with the interferer 1163 to interfere in a rotation of the winding member 1162. An indented portion may be formed on the fixing member 1164, and the indented portion may be provided in a shape corresponding to the interferer 1163. As an example, the indented portion of the fixing member 1164 may be provided in a form in contact with two of sides, for example, two sides facing each other, of the interferer 1163. By using the fixing member 1164, the rotation of the interferer 1163 may be restricted selectively.

As another example, the fixing member 1164 may fix a body of the winding member 1162 in lieu of the interferer 1163. For example, the fixing member 1164 may be combined with the opened portion of the winding member 1162.

The fixing member 1164 may slide and move in one direction in the adjustment body 1161. As an example, a guide groove may be formed on one side of the fixing member 1164. Also, a protrusion member may be formed on the adjustment body 1161 to be inserted to the guide groove. Based on the aforementioned configuration, the fixing member 1164 may slide and move in one direction. As another example, a separate bolt member may be provided to be inserted to the guide groove and connect the fixing member 1164 and the adjustment body 1161. On the adjustment body 1161, an interference wall may be formed to interfere with at least a portion of an external surface of the fixing member 1164. By using the interference wall, the fixing member 1164 may slide and move in a direction along which the guide groove is formed and may be prevented from sliding and moving in another direction.

A state in which the fixing member 1164 is in contact with the winding member 1162 by moving toward the winding member 1162 may also be referred to as, for example, a coupled state. When the fixing member 1164 is coupled with the winding member 1162, a winding of the winding member 1162 may be restricted.

A state in which the fixing member 1164 is spaced apart from the winding member 1162 by moving to an opposite side of the winding member 1162 may also be referred to as, for example, a released state. When the fixing member 1164 is released from the winding member 1162, the winding member 1162 may wind such that a length of the power transmission unit 115 is adjusted.

As illustrated in FIGS. 5A and 5B, the tensile force adjustment unit 116 including a plurality of fixing members 1164 and a plurality of winding members 1162. For example, each of the plurality of the fixing members 1164 may be configured to engage with a corresponding one of the winding members 1162*a* and 1162*b*.

The winding members 1162 may be disposed internally to both sides of the adjustment body 1161 based on a column formed on a center of the adjustment body 1161. At least a portion of both sides of the adjustment body 1161 may be opened such that the power transmission unit 115 is coupled with the winding member 1162.

A portion of the winding member 1162 may protrude from an upper portion of the adjustment body 1161. The winding member 1162 may include the interferer 1163 having a cross-sectional shape of a polygon, and the interferer 1163 may be disposed on an upper portion of the winding member 1162. When the body of the winding member 1162 is inserted to the adjustment body 1161, the interferer 1163 may be coupled with the body of the winding member 1162 on the upper portion of the adjustment body 1161. Alternatively, the interferer 1163 and the body of the winding member 1162 may be included in a single body.

A recessed portion 1165 may be formed on the upper portion of the adjustment body 1161 and the interferer 1163 and the fixing member 1164 may be disposed in the recessed portion 1165 such that the fixing member 1164 slides and moves in the recessed portion 1165.

The fixing member 1164 may be formed in a shape corresponding to a shape of the recessed portion 1165. In this example, when the fixing member 1164 moves to one side, an end portion of the fixing member 1164 may come into contact with one side of the recessed portion 1165 and thus, a movement of the fixing member 1164 may be restricted.

Contact sides of a plurality of fixing members 1164 may be formed to correspond to one another. The contact sides on which the plurality of fixing members 1164 is in contact with one another may be formed identically. For example, the contact side may be formed diagonally. A first fixing member may be provided in a form in which an upper length is greater than a lower length, and a second fixing member may be provided in a form in which an upper length is correspondingly less than a lower length. The plurality of fixing members 1164 may be disposed symmetrically to one another for a point.

The power transmission unit 115 may include a plurality of power transmission units, for example, a first power transmission unit 115*a* and a second power transmission unit 115*b*. The first power transmission unit 115*a* and the second power transmission unit 115*b* may be coupled with a first winding member 1162*a* and a second winding member 1162*b*, respectively. The first winding member 1162*a* and the second winding member 1162*b* may independently operate to selectively adjust the tensile force of the plurality of power transmission units.

Figure 6:
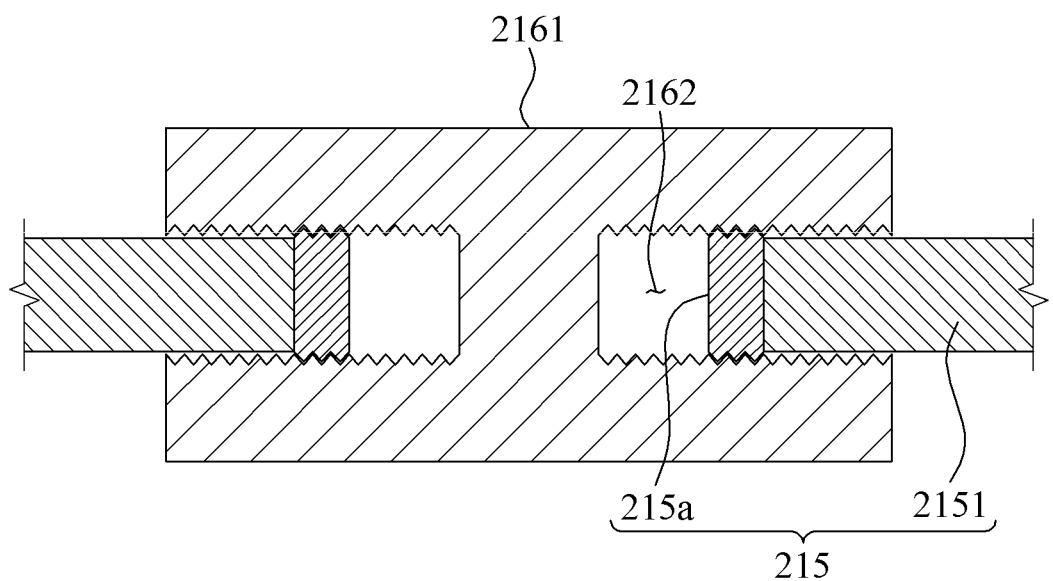
FIG. 6 is a cross-sectional view illustrating a tensile force adjustment unit according to example embodiments.

FIG. 6 is a cross-sectional view illustrating a tensile force adjustment unit 216 according to other example embodiments.

Referring to FIG. 6, the tensile force adjustment unit 216 may include an adjustment body 2161 to which a power transmission unit 215 is to be inserted. An insertion portion 2162 may be provided in at least one side of the adjustment body 2161, and a screw thread may be formed on the insertion portion 2162. The insertion portion 2162 may be provided on one or both sides of the adjustment body 2161.

Also, the insertion portion 2162 may be provided in a form penetrating the adjustment body 2161.

The power transmission unit 215 may include a power transmission body 2151 and an insertion body 215a attached to one side of the power transmission body 2151. A screw thread corresponding to the screw thread of the insertion portion 2162 may be formed on the insertion body 215a.

For example, a first tensile force adjustment screw thread, which is a female screw thread, may be formed on the insertion portion 2162, and a second tensile force adjustment screw thread, which is a male screw thread, may be formed on the insertion body 215a.

As illustrated in FIG. 6, the tensile force adjustment unit 216 may have insertion portions 2162 formed on both sides of the adjustment body 2161. By rotating the power transmission body 2151 or rotating the adjustment body 2161, the power transmission body 2151 may be moved to an inside or an outside of the adjustment body 2161. For example, when the adjustment body 2161 rotates in one direction, two insertion bodies 215a may be simultaneously inserted toward a center of the adjustment body 2161. When the adjustment body 2161 rotates in another direction, the two insertion bodies 215a may simultaneously move in a direction to be farther from the center of the adjustment body 2161. However, example embodiments are not limited thereto.

Figure 7:
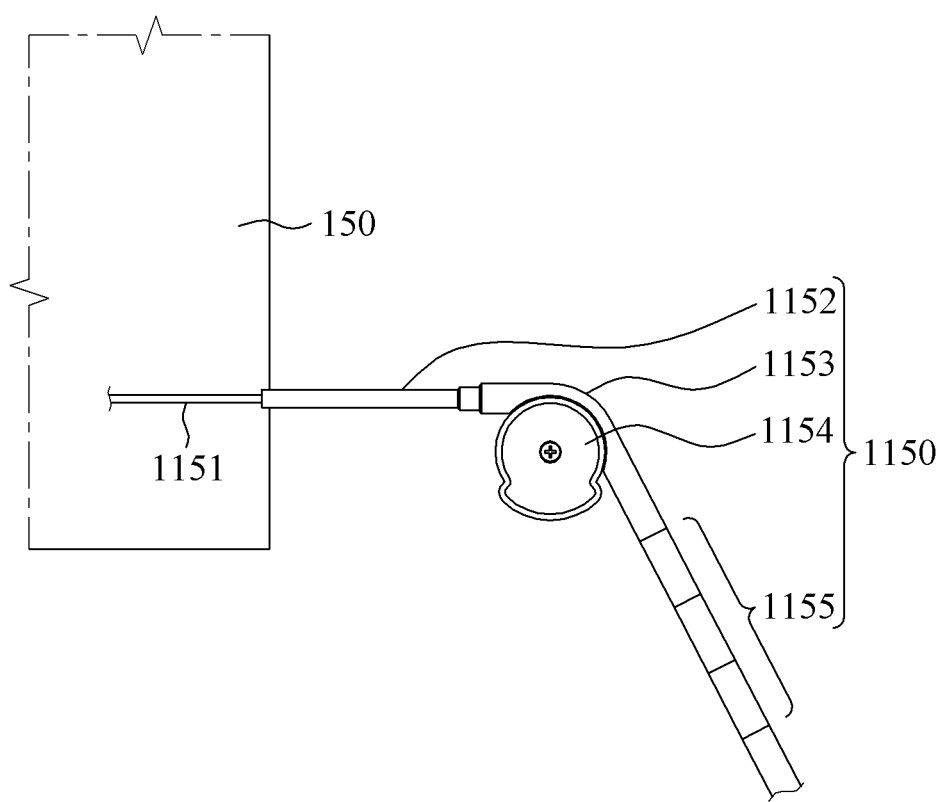
FIG. 7 illustrates a power transmission unit according to example embodiments.

FIG. 7 illustrates the power transmission unit 115 according to example embodiments.

Referring to FIG. 7, the power transmission unit 115 may include the power transmission body 1151 and a protection unit 1150.

The power transmission body 1151 may include, for example, a wire, a cable, a string, a rubber band, a spring, a belt, and a chain. The protection unit 1150 may include a shaft 1152, a bent pipe 1153, a rotary pulley 1154, and a surface body 1155. However, example embodiments are not limited thereto.

The shaft 1152 may include a flexible material. The shaft 1152 may cover a portion of the power transmission body 1151, and the power transmission body 1151 may move in the shaft 1152. The shaft 1152 may be disposed to be in contact with an external surface of box body 150 covering a portion of the driving module 110.

The rotary pulley 1154 may be disposed in a bent portion of the power transmission body 1151. For example, the rotary pulley 1154 may be disposed internally to the bent pipe 1153. The rotary pulley 1154 may be disposed in contact with the power transmission body 1151 to guide the power transmission body 1151 to smoothly move without sharply bending. The rotary pulley 1154 may include a bearing causing little friction. Also, a bushing may be provided in lieu of the rotary pulley 1154.

The bent pipe 1153 may include an accommodating space to accommodate the rotary pulley 1154 and cover at least a portion of the power transmission body 1151. The power transmission body 1151 may move in the bent pipe 1153. The bent pipe 1153 may include a material having a higher stiffness when compared to the shaft 1152. The rotary pulley 1154 may be inserted to the accommodating space to be fixed.

The surface body 1155 may cover at least a portion of the power transmission body 1151. The power transmission body 1151 may move in the surface body 1155. The surface body 1155 may be provided in a form of beads in which a plurality of segment portions fluidly connected to one another and thus, may have flexibility.

FIG. 7 illustrates an example of arranging the shaft 1152, the bent pipe 1153, and the surface body 1155 sequentially. For example, the shaft 1152 may be extended from an external surface of the box body 150. The bent pipe 1153 may be formed on one side of the shaft 1152. The bent pipe 1153 may be formed at an obtuse angle. The bent pipe 1153 may be coupled with the rotary pulley 1154. The rotary pulley 1154 may be fixed to the bent pipe 1153, thereby rotating in response to a driving of the power transmission body 1151. The surface body 1155 may be extended from one side of the bent pipe 1153. The surface body 1155 may be provided in a form in which a plurality of segment portions is connected.

The power transmission body 1151 may move in the shaft 1152, the bent pipe 1153, and the surface body 1155. Thus, the power transmission body 1151 may not be exposed externally to the box body 150.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A driving device comprising:
    a driving source configured to generate power;
    a rotary rod connected to the driving source, the rotary rod configured to rotate based on the power;
    a power conversion block coupled with the rotary rod, the power conversion block configured to perform a driving operation to drive in a straight-line in a longitudinal direction of the rotary rod in response to rotation of the rotary rod;
    a power transmitter configured to transmit the power in response to the driving operation of the power conversion block; and
    a tensile force adjustment device configured to connect the power conversion block and the power transmitter, and to adjust a tensile force of the power transmitter, the tensile force adjustment device including a winding member and a fixing member, the winding member configured to perform a rotation to wind the power transmitter therearound, and the fixing member configured to selectively couple with the winding member to selectively interfere in the rotation of the winding member.

2. The driving device of claim 1, wherein the power transmitter comprises:
    a first power transmitter and a second power transmitter, the first power transmitter and the second power transmitter configured to connect to the tensile force adjustment device, and wherein
        the winding member is configured to wind at least one of the first power transmitter and the second power transmitter therearound.

3. The driving device of claim 1, further comprising:
    a linear motion guide configured to guide a movement of the tensile force adjustment device.

4. The driving device of claim 1, further comprising:
    a timing belt configured to rotate based on the power generated by the driving source; and
    a rotary pulley configured to rotate the rotary rod in response to the rotation of the timing belt.

5. The driving device of claim 1, wherein
the rotary rod includes a first screw thread thereon, and
the power conversion block includes a second screw thread thereon, the second screw thread corresponding to the first screw thread.

6. A driving device comprising:
a driving source configured to generate rotational power;
a power converter configured to convert the rotational power into a linear motion;
a power transmitter configured to operate in response to the linear motion;
a guide member configured to guide a movement of a driving frame; and
a tensile force adjustment device configured to adjust a tensile force of the power transmitter, the tensile force adjustment device including,
    a winding member configured to perform a rotation to wind the power transmitter therearound, and
    a fixing member configured to selectively couple with the winding member to selectively interfere in the rotation of the winding member.

7. The driving device of claim 6, wherein
the winding member includes an interferer on an upper end thereof, the interferer having a polygonal shape, and
the fixing member includes an indented portion thereon, the indented portion having a shape corresponding to the interferer.

8. The driving device of claim 6, wherein
the tensile force adjustment device includes a recessed portion thereon, the recessed portion configured to accommodate the fixing member, and
the fixing member is configured to slide in one direction in the recessed portion.

9. The driving device of claim 6, wherein
the winding member includes a first winding member and a second winding member,
the power transmitter includes a first power transmission transmitter and a second power transmission transmitter, and
the first winding member is configured to couple with the first power transmission transmitter and the second winding member is coupled with the second power transmission transmitter.

10. The driving device of claim 9, wherein the fixing member comprises:
a first fixing member and a second fixing member, the first fixing member and the second fixing member configured to selectively couple with the first winding member and the second winding member, respectively.

11. A motion assistance apparatus comprising:
a fixing device configured to attach to a user, the fixing device including side frames and a dial, the side frames covering a circumference of the user, the dial configured to adjust a first distance between the side frames to set a width of the fixing device;
a driving device including,
    a driving frame,
    a driving source configured to generate power,
    a power transmitter configured to operate in response to the power, and
    a tensile force adjustment device configured to adjust a tensile force of the power transmitter, and
    a guide member configured to guide a movement of the driving frame to maintain a second distance between the driving frame and the joint in response changes in the first distance; and
a joint configured to assist a motion of the user.

12. The motion assistance apparatus of claim 11, wherein the joint is configured to assist a motion by receiving the power from the driving device via the power transmitter.

13. The motion assistance apparatus of claim 11, wherein the power transmitter further comprises:
a power transmission body; and
a protection unit formed on at least a portion of the power transmission body.

14. The motion assistance apparatus of claim 13, wherein the protection unit comprises:
a rotary pulley configured to rotate in response to a driving of the power transmission body.

15. The motion assistance apparatus of claim 14, wherein the protection unit comprises:
a bent pipe configured to cover at least a portion of the power transmission body, the bent pipe configured to accommodate the rotary pulley in a space therein.

16. The motion assistance apparatus of claim 13, wherein the protection unit comprises:
a flexible shaft configured to cover at least a portion of the power transmission body.

17. The motion assistance apparatus of claim 13, wherein the protection unit comprises:
a surface body configured to cover at least a portion of the power transmission body, the surface body including a plurality of segment portions, each of the plurality of segment portions fluidly connected to another one of the plurality of segment portions.

* * * * *